US012731676B2

(12) United States Patent
Ma et al.

(10) Patent No.: US 12,731,676 B2

(45) Date of Patent: Sep. 8, 2026

(54) SYSTEMS, METHODS, AND APPARATUSES FOR ACCRUING AND REUSING KNOWLEDGE (ARK) FOR SUPERIOR AND ROBUST PERFORMANCE BY A TRAINED AI MODEL FOR USE WITH MEDICAL IMAGE CLASSIFICATION

(71) Applicant: Arizona Board of Regents on behalf of Arizona State University, Scottsdale, AZ (US)

(72) Inventors: DongAo Ma, Tempe, CA (US); Jiaxuan Pang, Tempe, CA (US); Jianming Liang, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 260 days.

(21) Appl. No.: 18/627,831

(22) Filed: Apr. 5, 2024

(65) Prior Publication Data

US 2024/0339200 A1 Oct. 10, 2024

Related U.S. Application Data

(60) Provisional application No. 63/537,433, filed on Sep. 8, 2023, provisional application No. 63/457,649, filed on Apr. 6, 2023.

(51) Int. Cl.

*G06K 9/00* (2022.01)
*G06V 10/764* (2022.01)

(Continued)

(52) U.S. Cl.

CPC .......... *G16H 30/40* (2018.01); *G06V 10/764* (2022.01); *G16H 30/20* (2018.01)

(58) Field of Classification Search

CPC ...... G16H 30/40; G16H 30/20; G06V 10/764; G06V 10/82; G06V 2201/03

See application file for complete search history.

(56) References Cited

U.S. PATENT DOCUMENTS

| | | | | |
|---|---|---|---|---|
| 11,687,620 B2 * | 6/2023 | Avegliano | G06V 10/774 382/155 |
| 2023/0087292 A1 * | 3/2023 | Wang | G06N 3/096 382/159 |
| 2023/0106440 A1 * | 4/2023 | Golden | G06N 3/09 382/131 |

OTHER PUBLICATIONS

Sellergren, Andrew B., et al. "Simplified transfer learning for chest radiography models using less data." Radiology 305.2 (2022): 454-465.*

(Continued)

*Primary Examiner* — Avinash Yentrapati

(74) *Attorney, Agent, or Firm* — Elliott, Ostrander & Preston, P.C.

(57) ABSTRACT

Exemplary systems include means for receiving medical image data at the system from a plurality of datasets provided via publicly available sources; evaluating the medical image data for the presence of expert notation embedded within the medical image data; determining the expert notations embedded within the medical image data are formatted using inconsistent and heterogeneous labeling across the plurality of datasets; generating an interim AI model by applying a task head classifier to learn the annotations of the expert notations embedded within the medical image data to generate an interim AI model; scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objec- (Continued)

tives; training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

9 Claims, 3 Drawing Sheets

(51) Int. Cl.
*G16H 30/20* (2018.01)
*G16H 30/40* (2018.01)

(56) References Cited

OTHER PUBLICATIONS

Smith, Leslie N. “General cyclical training of neural networks.” arXiv preprint arXiv:2202.08835 (2022).*

Xie, Z. et al., “SimMIM: A Simple Framework for Masked Image Modeling,” Proceedings of the IEEE/CVF Conference on Computer Vision and Pattern Recognition (CVPR), 2022, pp. 9653-9663.

Johnson, Alistair EW, et al. “MIMIC-CXR, a de-identified publicly available database of chest radiographs with free-text reports.” Scientific data 6.1 (2019): 317.

Kemker, Ronald, et al. “Measuring catastrophic forgetting in neural networks.” Proceedings of the AAAI conference on artificial intelligence. vol. 32. No. 1. 2018.

Larrazabal, Agostina J., et al. “Gender imbalance in medical imaging datasets produces biased classifiers for computer-aided diagnosis.” Proceedings of the National Academy of Sciences 117.23 (2020): 12592-12594.

Liu, Z., Lin, Y., Cao, Y., Hu, H., Wei, Y., Zhang, Z., . . . & Guo, B. (2021). Swin transformer: Hierarchical vision transformer using shifted windows. In Proceedings of the IEEE/CVF international conference on computer vision (pp. 10012-10022).

Liu, Jie, et al. “Clip-driven universal model for organ segmentation and tumor detection.” Proceedings of the IEEE/CVF international conference on computer vision. 2023.

Ma, DongAo, et al. “Benchmarking and boosting transformers for medical image classification.” MICCAI Workshop on Domain Adaptation and Representation Transfer. Cham: Springer Nature Switzerland, 2022.

Ma, DongAo, et al. “Foundation ark: Accruing and reusing knowledge for superior and robust performance.” International Conference on Medical Image Computing and Computer-Assisted Intervention. Cham: Springer Nature Switzerland, 2023.

McMahan, Brendan, et al. “Communication-efficient learning of deep networks from decentralized data.” Artificial intelligence and statistics. PMLR, 2017.

Nguyen, Hoang C., et al. “VinDr-RibCXR: A benchmark dataset for automatic segmentation and labeling of individual ribs on chest X-rays.” arXiv preprint arXiv:2107.01327 (2021).

Nguyen, Ha Q., et al. “VinDr-CXR: An open dataset of chest X-rays with radiologist’s annotations.” Scientific Data 9.1 (2022): 429.

Peng, Yifan, et al. “NegBio: a high-performance tool for negation and uncertainty detection in radiology reports.” AMIA Summits on Translational Science Proceedings 2018 (2018): 188.

Shiraishi, Junji, et al. “Development of a digital image database for chest radiographs with and without a lung nodule: receiver operating characteristic analysis of radiologists’ detection of pulmonary nodules.” American journal of roentgenology 174.1 (2000): 71-74.

“SIIM-ACR Pneumothorax Segmentation” (Online) (2019), https://www.kaggle.com/c/siim-acr-pneumothorax-segmentation/, 26 pages.

Tarvainen, Antti, and Harri Valpola. “Mean teachers are better role models: Weight-averaged consistency targets improve semi-supervised deep learning results.” Advances in neural information processing systems 30 (2017).

Wang, X., Peng, Y., Lu, L., Lu, Z., Bagheri, M., & Summers, R. M. (2017). Chestx-ray8: Hospital-scale chest x-ray database and benchmarks on weakly-supervised classification and localization of common thorax diseases. In Proceedings of the IEEE conference on computer vision and pattern recognition (pp. 2097-2106).

Xiao, Tete, et al. “Unified perceptual parsing for scene understanding.” Proceedings of the European conference on computer vision (ECCV). 2018.

Zhang, Jianpeng, et al. “Dodnet: Learning to segment multi-organ and tumors from multiple partially labeled datasets.” Proceedings of the IEEE/CVF conference on computer vision and pattern recognition. 2021.

Zhu, Zengle, et al. “Assembling existing labels from public datasets to diagnose novel diseases: Covid-19 in late 2019.” NeurIPS Workshop on Medical Imaging meets NeurIPS. 2022.

Colak, Errol, et al. “The RSNA pulmonary embolism CT dataset.” Radiology: Artificial Intelligence 3.2 (2021): e200254.

Jaeger, S., Candemir, S., Antani, S., Wáng, Y. X. J., Lu, P. X., & Thoma, G. (2014). Two public chest X-ray datasets for computer-aided screening of pulmonary diseases. Quantitative imaging in medicine and surgery, 4(6), 475.

Irvin, J., Rajpurkar, P., Ko, M., Yu, Y., Ciurea-Ilcus, S., Chute, C., . . . & Ng, A. Y. (2019, July). Chexpert: A large chest radiograph dataset with uncertainty labels and expert comparison. In Proceedings of the AAAI conference on artificial intelligence (vol. 33, No. 01, pp. 590-597).

* cited by examiner

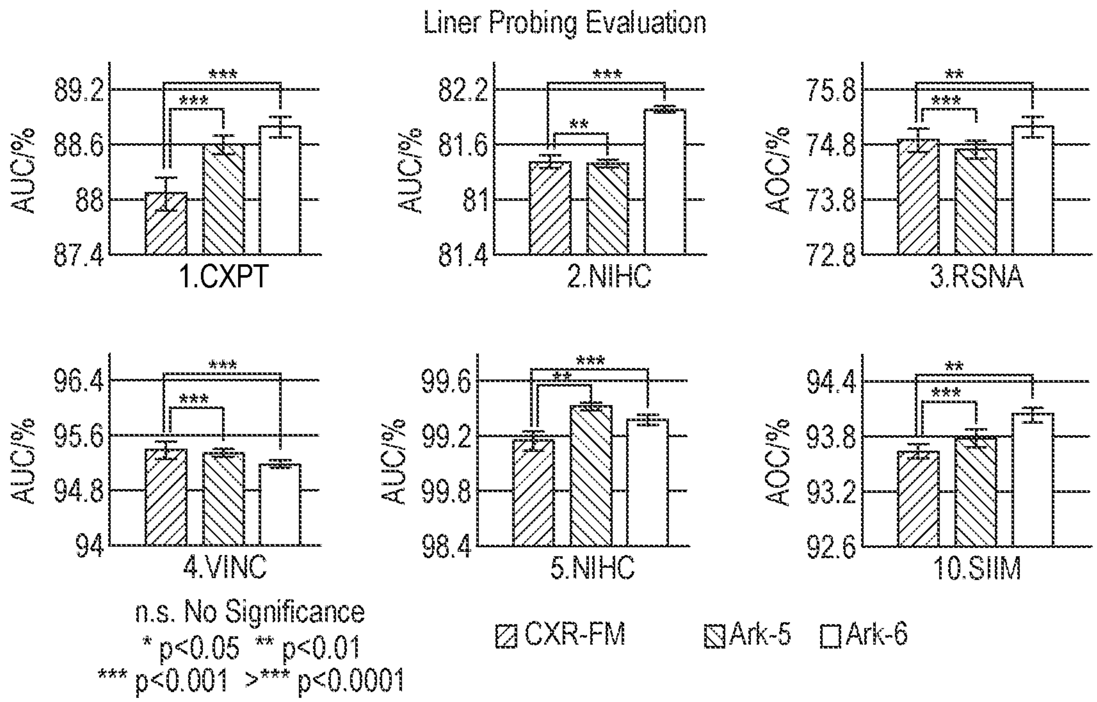
FIG. 2A
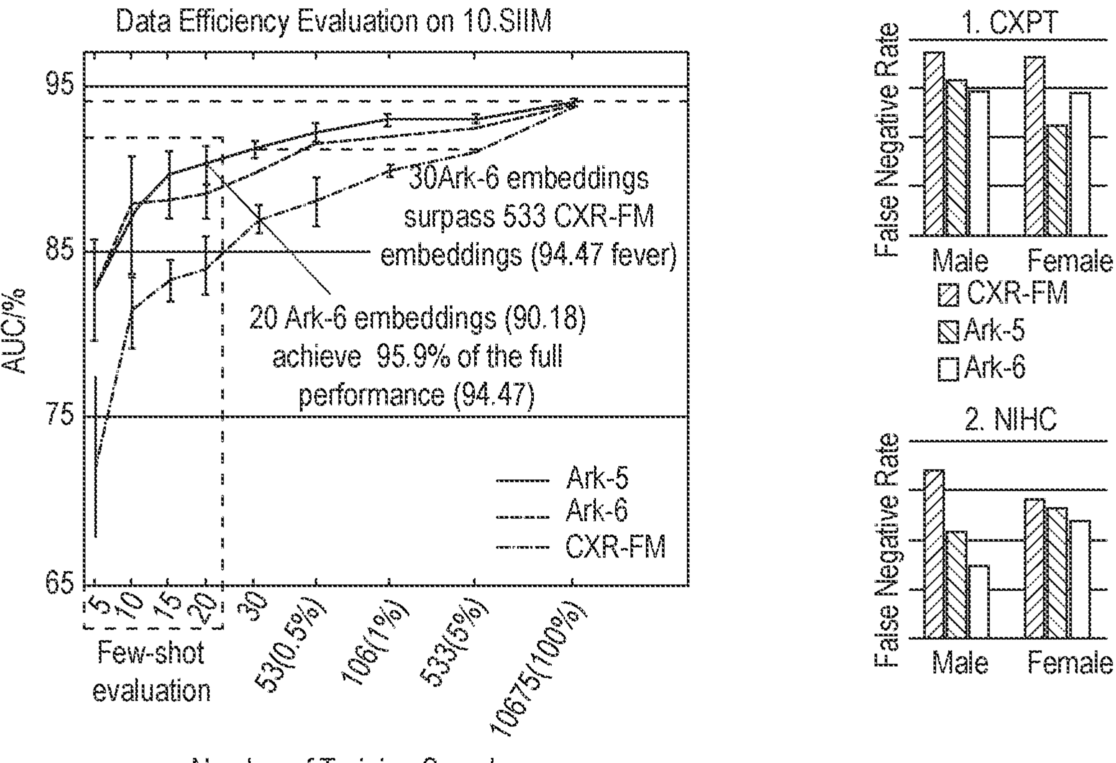
FIG. 2B
FIG. 3A

SYSTEMS, METHODS, AND APPARATUSES FOR ACCRUING AND REUSING KNOWLEDGE (ARK) FOR SUPERIOR AND ROBUST PERFORMANCE BY A TRAINED AI MODEL FOR USE WITH MEDICAL IMAGE CLASSIFICATION

CLAIM OF PRIORITY

This application claims the benefit of U.S. Provisional Patent Application No. 63/457,649, filed Apr. 6, 2023, entitled "SYSTEMS, METHODS, AND APPARATUSES FOR ACCRUING AND REUSING KNOWLEDGE (ARK) TO ATTAIN SUPERIOR AND ROBUST PERFORMANCE BY A TRAINED AI MODEL FOR USE WITH MEDICAL IMAGE CLASSIFICATION", the disclosure of which is incorporated by reference herein in its entirety. This application claims the benefit of U.S. Provisional Patent Application No. 63/537,433, filed Sep. 8, 2023, entitled "SYSTEMS, METHODS, AND APPARATUSES FOR ACCRUING AND REUSING KNOWLEDGE (ARK) TO ATTAIN SUPERIOR AND ROBUST PERFORMANCE BY A TRAINED AI MODEL FOR USE WITH MEDICAL IMAGE CLASSIFICATION", the disclosure of which is incorporated by reference herein in its entirety.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks and transformers for the classification and annotation of medical images, and more particularly, to systems, methods, and apparatuses for Accruing and Reusing Knowledge (ARK) for superior and robust performance by a trained AI model for use with medical image classification, in the context of medical image analysis.

BACKGROUND

The subject matter discussed in the background section should not be assumed to be prior art merely because of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Unfortunately, prior known techniques in both self-supervised and fully supervised models require consistent and repeatable data annotation.

What is needed is an improved technique for leveraging the expert knowledge already present within medical imagery, but presented in the format of heterogeneous labels via which to accrue and reuse available but inconsistent data.

The present state of the art may therefore benefit from the systems, methods, and apparatuses for Accruing and Reusing Knowledge (ARK) to attain superior and robust performance by a trained AI model for use with medical image classification, as described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 2A depicts embodiments of the invention, referred to herein as Ark-5 and Ark-6, compared with Google CXR-FM via linear probing with a complete training set on six target tasks, demonstrating Ark's superior or comparable performance and better embedding quality;

FIG. 2B depicts embodiments of the invention, referred to herein as Ark-5 and Ark-6, compared with partial training sets or even few-shot samples, showcasing Ark's outstanding performance in terms of data efficiency;

FIG. 3A illustrates that Ark models have lower FNRs than CXR-FM for both genders on both tasks, demonstrating that Ark models are less likely to underdiagnose disease conditions than CXR-FM.

DETAILED DESCRIPTION

Figure 1:
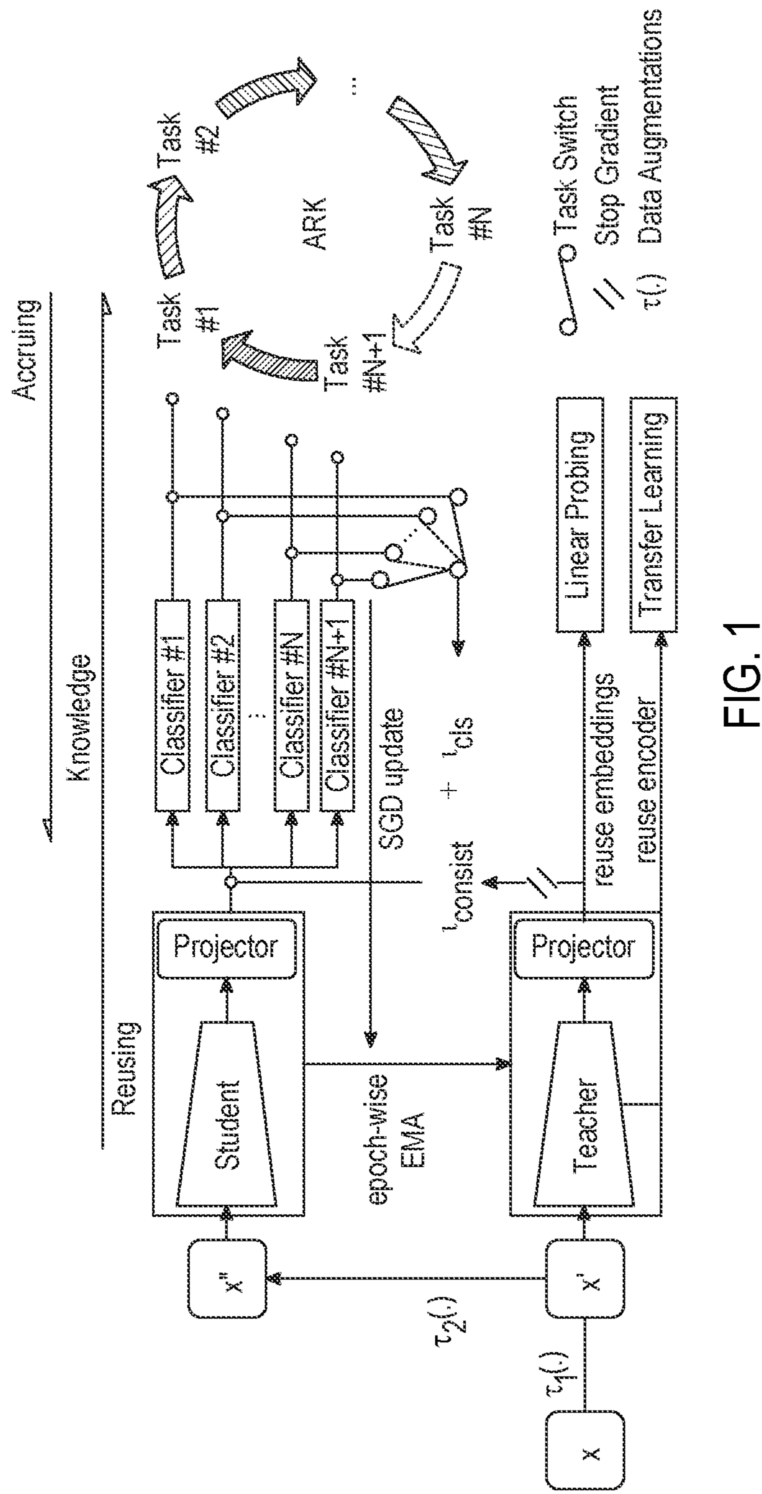
FIG. 1 depicts embodiments of the invention built on a student-teacher model with multi-task heads and trained via cyclic pretraining, aiming to accrue and reuse the expert knowledge embedded in the heterogeneous labels with numerous public datasets.

Described herein are systems, methods, and apparatuses for accruing and re-using knowledge (ARK) for superior and robust performance by a trained AI model for use with medical image classification, in the context of medical image analysis.

Deep learning nowadays offers expert-level and sometimes even super-expert-level performance, but achieving such performance demands massively annotated data for training (e.g., Google's proprietary CXR Foundation Model (CXR-FM) was trained on 821,544 labeled and mostly private chest X-rays (CXRs)). Numerous datasets are publicly available in medical imaging but individually small and heterogeneous in expert labels. Embodiments of the invention contemplate a powerful and robust foundation model that can be trained by aggregating numerous small public datasets. To realize this vision, embodiments of the invention, i.e., "ARK", or "Ark", provide a framework that accrues and reuses knowledge from heterogeneous expert annotations in various datasets. As a proof of concept, two Ark models have been trained on 335,484 and 704,363 CXRs, respectively, by merging several datasets including ChestX-ray14, CheXpert, MIMIC-II, and VinDr-CXR, which were evaluated on a wide range of imaging tasks covering both classification and segmentation via fine-tuning, linear-probing, and gender-bias analysis, demonstrating Ark's superior and robust performance over the state-of-the-art (SOTA) fully/self-supervised baselines and Google's proprietary CXR-FM. This enhanced performance is attributed to the observation that aggregating numerous public numerous small public datasets. To test this hypothesis, CXRs have been chosen because they are one of the most frequently used modalities, and the research community has accumulated copious CXRs (see Table 1). However, annotations associated with these public datasets are inconsistent in disease coverage. Even when addressing the same clinical issue, datasets created at different institutions tend to be annotated differently. For example, VinDr-CXR is associated with global (image-level) and local (boxed-lesions) labels, while MIMIC-CXR has no expert labels per se but comes with radiology reports. ChestX-ray14 and CheXpert both cover 14 conditions at the image level, and their 14 conditions have overlaps but are not exactly the same. Therefore, embodiments of the invention seek to address a critical need: How to utilize numerous publicly available images from different sources and their readily accessible but heterogeneous expert annotations to pretrain generic source (foundation) models that are more robust and transferable to application-specific target tasks.

Table 1 identifies publicly available datasets that are generally small and heterogeneously annotated. Ark (FIG. 1) aims to aggregate numerous datasets with heterogeneous annotations to diversify patient population, accrue knowledge from diverse experts, and meet the demand by deep learning for massively annotated training data, offering superior and robust performance (Table 2, FIGS. 2A, 2B and 3A, 3B) yet reducing annotation cost.

TABLE 1

| Abbrev. | Dataset | Task | Usage* | (Pre)train/val/test |
|---|---|---|---|---|
| 1. CXPT | CheXpert [4] | classify 14 thoracic diagnosis | P\|F\|L\|B | 223414/—/234 |
| 2. NIHC | NIH ChestX-ray14 [19] | classify 14 thoracic diseases | P\|F\|L\|B | 75312/11212/25596 |
| 3. RSNA | RSNA Pneumonia [1] | classify lung opacity, abnormality | P\|F\|L | 21295/2680/2709 |
| 4. VINC | VinDr-CXR [13] | classify 6 thoracic diagnosis | P\|F\|L | 15000/—/3000 |
| 5. NIHS | NIH Shenzhen CXR [5] | classify tuberculosis | P\|F\|L | 463/65/134 |
| 6. MMIC | MIMIC-II [6] | classify 14 thoracic diagnoses† | P | 368879/2992/5159 |
| 7. NIHM | NIH Montgomery [5] | segment lungs | P | 92/15/31 |
| 8. JSRT | JSRT [17] | segment lungs, heart, clavicles | P | 178/25/49 |
| 9. VINR | VinDr-RibCKR [14] | segment 20 ribs | P | 196/—/49 |
| 10. SIIM | SIIM-ACR PTX [2] | classify pneumothorax‡ | L | 10675/—/1372 |

*The usage of each dataset in our experiments is denoted with P for pretraining, F for fine-tuning, L for linear probing, and B for bias study.
†The labels of CX Rs in MIMIC-II are derived from their corresponding radiology reports using NegBio [15] and CheXpert [4].
‡SIIM-ACR, originally for pneumothorax segmentation, is converted into a classification task for linear probing, as CX R datasets diversifies patient populations and accrues knowledge from diverse experts, yielding unprecedented performance yet saving annotation cost. With this disclosure it is hoped that Ark exerts an important impact on open science, as accruing and reusing knowledge from expert annotations in public datasets can potentially surpass the performance of proprietary models trained on unusually large data, inspiring many more researchers worldwide to share codes and datasets to build open foundation models, accelerate open science, and democratize deep learning for medical imaging.

1. Introduction

Figure 3B:
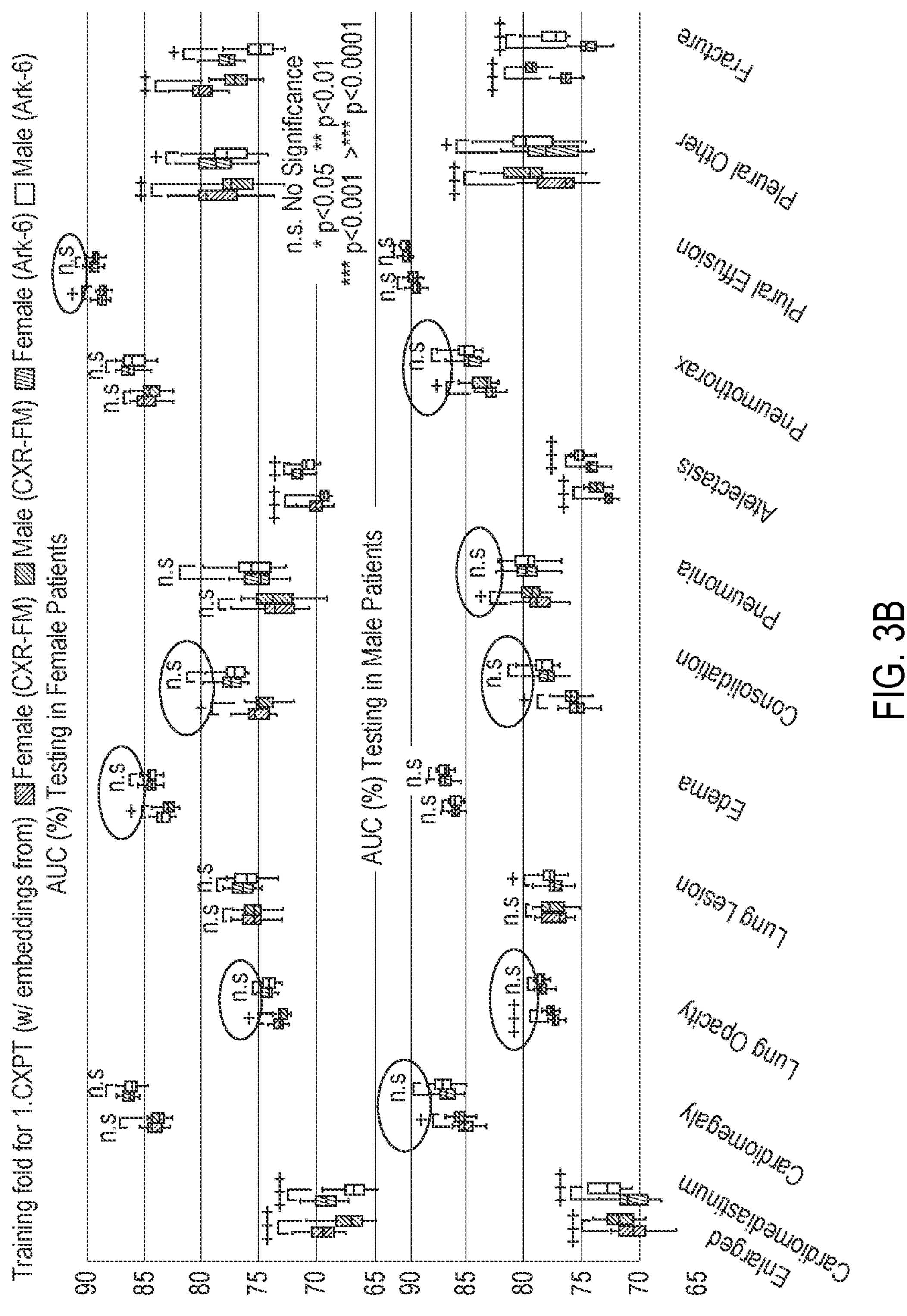
FIG. 3B illustrates the biases in the pretrained models are measured by performance differences between linear classifiers trained on male-only and female-only embeddings, according to embodiments.

Deep learning today offers expert-level and sometimes even higher-level performance, deepening and widening its applications in medical imaging and resulting in numerous public datasets for research, competitions, and challenges. These datasets are generally small as annotating medical images is challenging, but achieving superior performance by deep learning demands massively annotated data for training. For example, Google's proprietary CXR Foundation Model (CXR-FM) was trained on 821,544 labeled and mostly private CXRs. It is thought that powerful and robust open foundation models can be trained by aggregating To address this need, embodiments of the invention provide a framework, called Ark, because of its ability of accruing and reusing knowledge embedded in heterogeneous expert annotations with numerous datasets, as illustrated in FIG. 1, which depicts Ark built on a student-teacher model with multi-task heads and trained via cyclic pretraining, aiming to accrue and reuse the expert knowledge embedded in the heterogeneous labels with numerous public datasets (see section 2 for details). Models pretrained with Ark are referred to as Foundation Ark or simply as Ark for short. To demonstrate Ark's capability, two models have been trained: Ark-5 on Datasets 1-5 and Ark-6 on Datasets 1-6 (Table 1); and evaluated on a wide range of ten tasks via fine-tuning and on six tasks via linear probing, demonstrating that Ark models outperform the SOTA fully/self-supervised baselines (Table 2) and Google CXR-FM1 (FIG. 2A, 2B). Ark also exhibits superior robustness over CXR-FM in mitigating underdiagnosis and reducing gender-related biases, with lower false-negative rates and greater robustness to imbalanced data (FIG. 3A, 3B).

This performance enhancement is attributed to the observation that aggregating numerous public datasets costs nearly nothing but enlarges data size, diversifies patient populations, and accrues expert knowledge from many sources worldwide, thereby offering unprecedented performance yet reducing annotation cost. More important, Ark is fundamentally different from self-supervised learning (SSL) and federated learning (FL) in concept. SSL can naturally handle images from different sources, but their associated expert annotations are left out of pretraining. Every bit of expert annotation counts, conveying valuable knowledge. FL can utilize data with annotations from different sources, typically involving homogeneous labels, but it mainly concerns data privacy. By contrast, Ark focuses on heterogeneous expert annotations with public data with no concern for data privacy and employs centralized training, which usually offers better performance with the same amount of data and annotation than distributed training as in FL.

The embodiments and associated work provide the following contributions: (1) aggregate public datasets to enlarge and diversify training data; (2) using a student-teacher model with multi-task heads via cyclic pretraining that accrues expert knowledge from existing heterogeneous annotations to achieve superior and robust performance yet reduce annotation cost; (3) comprehensive experiments that evaluate Ark via fine-tuning, linear-probing, and few-shot learning on a variety of target tasks, demonstrating Ark's better generalizability and transferability in comparison with SOTA methods and Google CXR-FM; and (4) empirical analyses for robustness to underdiagnosis and gender imbalance in medical imaging models, highlighting Ark significantly enhances reliability and safety in clinical decision-making.

2. Accruing and Reusing Knowledge

Ark aims to learn superior and robust visual representations from large-scale aggregated medical images by accruing and reusing the expert knowledge embedded in all available heterogeneous labels. The following discussion provides further details regarding Ark.

Accruing knowledge into the student via cyclic pretraining. A significant challenge with training a single model using numerous datasets created for different tasks is label inconsistency (i.e., heterogeneity) (see Table 3). Manually consolidating heterogeneous labels from different datasets would be a hassle. To circumvent this issue, for each task, a specific classifier, called task head, is introduced to learn from its annotation and encode the knowledge into the model. A task head can be easily plugged into Ark, making Ark scalable to additional tasks. With multi-task heads, Ark can learn from multiple tasks concurrently or cyclically. In concurrent pretraining, a mini-batch is formed by randomly sampling an equal number of images from each dataset, and the loss for each image is computed based on its associated dataset identifier (ID) and labels. This idea is intuitive, but the model hardly converges; it is suspected that the loss summation over all task heads simultaneously weakens gradients for back-propagation, causing confusion in weight updating. Embodiments opt for cyclic pre-training by iterating through all datasets sequentially in each round to accrue expert knowledge from all available annotations, a strategy that has been found to stabilize Ark's pretraining and accelerates its convergence.

Accruing knowledge into the teacher via epoch-wise exponential moving average (EMA). To further summarize the accrued knowledge and accumulate the learning experiences in the historical dimension, Ark is introduced as a teacher model that shares the same architecture with the student. The teacher is updated using (EMA) based on the student's one epoch of learning at the end of each task. Eventually, the expert knowledge embedded in all labels and all historical learning experiences are accrued in the teacher model for further reuse in the cyclic pretraining and for future application-specific target tasks.

Reusing accrued knowledge from the student to bolster cyclic pre-training. If the model learns from multiple tasks sequentially, it may "forget" the previously learned knowledge, and its performance on an old task may degrade catastrophically. This problem is addressed naturally in Ark by cyclic pretraining, where the model revisits all the tasks in each round and reuses all knowledge accrued from the previous rounds and tasks to strengthen its learning from the current and future tasks. That is, by regularly reviewing the accrued knowledge through task revisitation, Ark not only prevents forgetting but also enables more efficient and effective learning from multiple tasks iteratively.

Reusing accrued knowledge from the teacher to mitigate forgetting. To leverage the accumulated knowledge of the teacher model as an additional self-supervisory signal, a consistency loss between the student and the teacher is incorporated, as shown in FIG. 1. To enhance this supervision, projectors are introduced in Ark that map the outputs of the student and teacher encoders to the same feature space. This further reinforces the feedback loop between the student and teacher models, facilitating the transfer of historical knowledge from the teacher to the student as a reminder to mitigate forgetting.

Ark has the following properties:

Knowledge-centric. Annotating medical images by radiologists for deep learning is a process of transferring their in-depth knowledge and expertise in interpreting medical images and identifying abnormalities to a medium that is accessible for computers to learn. Ark's superior and robust performance is attributed to the accumulation of expert knowledge conveyed through medical imaging annotations from diverse expert sources worldwide. At the core of Ark is acquiring and sharing knowledge: "knowledge is power" (Mac Flecknoe) and "power comes not from knowledge kept but from knowledge shared" (Bill Gates).

Label-agnostic, task-scalable and annotation-heterogeneous. Ark is label agnostic as it does not require prior label "understanding" of public datasets, but instead uses their originally provided labels. It is designed with pluggable multi-task heads and cyclic pretraining to offer flexibility and scalability for adding new tasks without manually consolidating heterogeneous labels or training task-specific controllers/adapters. Therefore, Ark intrinsically handles the annotation heterogeneity across different datasets.

Application-versatile. Ark trains versatile foundation models by utilizing a large number of publicly available images from diverse sources and their readily accessible diagnostic labels. As shown in section 3, Ark models are more robust, generalizable, and transferable to a wide range of application-specific target tasks across diseases (e.g., pneumothorax, tuberculosis, cardiomegaly) and anatomies (e.g., lung, heart, rib), highlighting Ark's versatility.

Thus, embodiments of the invention include a system comprising a memory to store instructions, a processor to execute the instructions stored in the memory, wherein the system is specially configured to execute instructions for accruing and reusing knowledge by a trained artificial intelligence (AI) model for use with medical image classification, in the context of medical image analysis, by performing the following operations: receiving medical image data at the system from a plurality of datasets provided via publicly available sources; evaluating the medical image data for the presence of expert notation embedded within the medical image data; determining the expert notations embedded within the medical image data are formatted using inconsistent and heterogeneous labeling across the plurality of datasets; generating an interim AI model by applying a task head classifier to learn the annotations of the expert notations embedded within the medical image data to generate an interim AI model; scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objectives; and training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

According to embodiments, the system further provides instructions for generating a new pre-trained AI model specially configured for a new application-specific target task by applying cyclic training of the new pre-trained AI model for the new application-specific target task, wherein the cyclic training iteratively repeats the training of the pre-trained AI model previously trained against the first application-specific target task.

According to embodiments, model degradation is mitigated by re-applying task re-visitation training forcing the new pre-trained AI model being trained to re-visit all tasks in each round of training and forcing the new pre-trained AI model being trained to re-use all accrued knowledge to improve learning by the first pre-trained AI model for the first application-specific target task as improving learning for the new pre-trained AI model specifically configured for the new application-specific target task.

Embodiments of the invention further include a computer-implemented method performed by a system having at least a processor and a memory therein to execute instructions for accruing and reusing knowledge by a trained artificial intelligence (AI) model for use with medical image classification, in the context of medical image analysis, by performing the following operations: receiving medical image data at the system from a plurality of datasets provided via publicly available sources; evaluating the medical image data for the presence of expert notation embedded within the medical image data; determining the expert notations embedded within the medical image data are formatted using inconsistent and heterogeneous labeling across the plurality of datasets; generating an interim AI model by applying a task head classifier to learn the annotations of the expert notations embedded within the medical image data to generate an interim AI model; scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objectives; and training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

Finally, embodiments include a non-transitory computer readable storage media having instructions stored thereupon that, when executed by a system having at least a processor and a memory therein, the instructions cause the processor to execute instructions for accruing and reusing knowledge by a trained artificial intelligence (AI) model for use with medical image classification, in the context of medical image analysis, by performing the following operations: receiving medical image data at the system from a plurality of datasets provided via publicly available sources; evaluating the medical image data for the presence of expert notation embedded within the medical image data; determining the expert notations embedded within the medical image data are formatted using inconsistent and heterogeneous labeling across the plurality of datasets; generating an interim AI model by applying a task head classifier to learn the annotations of the expert notations embedded within the medical image data to generate an interim AI model; scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objectives; and training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

3. Experiments and Results

Ark-5 and Ark-6 take the base version of the Swin transformer (Swin-B) as the backbone, feature five and six independent heads based on the pretraining tasks and their classes, and are pretrained on Datasets 1-5 and 1-6, respectively, with all validation and test data excluded to avoid test-image leaks. In the following description, both models are evaluated via transfer learning (in sections 3.1 and 3.2) on a wide range of ten common, yet challenging, tasks on eight publicly available datasets, encompassing various thoracic diseases and diverse anatomy. To provide a more comprehensive evaluation, linear probing is conducted (in section 3.3) and gender biases analyzed (in section 3.4) on the Ark models in comparison with Google CXR-FM. Pretraining and evaluation protocols are detailed in the supplementary material provided below.

1) Ark Outperforms SOTA Fully/Self-Supervised Methods on Various Tasks for Thoracic Disease Classification.

Experimental Setup: To demonstrate the performance improvements achieved through Ark pretraining, Ark models were compared with SOTA fully supervised and self-supervised models that were pretrained on ImageNet. A comparison is provided below with a SOTA domain-adapted model that was first pretrained on ImageNet and then on a large-scale domain-specific dataset comprising 926,028 CXRs from 13 different sources. All downstream models share the same Swin-B backbone, where the encoder is initialized using the pretrained weights and a task-specific classification head is re-initialized based on the number of classes for the target task. All layers in the downstream models are fine-tuned under the same experimental setup. The results of training the downstream models from scratch (random initialization) as the performance lower bound is also reported. Note that Google CXR-FM cannot be included for comparison as it is not publicly released for fine-tuning.

Table 2 depicts Ark-5 and Ark-6 outperforming SOTA ImageNet pretrained models and the self-supervised domain-adapted model that utilizes even more training data, highlighting the importance of accruing and reusing knowledge in expert labels from diverse datasets for both classification and segmentation. With the best bolded and the second best underlined, a statistical analysis is conducted between the best vs. others, where boxes indicate no statistically significant difference at level p=0.05.

TABLE 2

| | | Classification task | | | | |
|---|---|---|---|---|---|---|
| Initialization | Pretraining | 1.CXPT | 2.NIHC | 3.RSNA | 4.VINC | 5.NIHS |
| Random | — | 83.39 ± 0.84 | 77.04 ± 0.34 | 70.02 ± 0.42 | 78.49 ± 1.00 | 92.52 ± 4.98 |
| Supervised | IN | 87.89 ± 0.42 | 81.73 ± 0.14 | 73.44 ± 0.46 | 90.35 ± 0.31 | 93.35 ± 0.77 |
| SimMIM | IN | 88.16 ± 0.31 | 81.95 ± 0.15 | 73.66 ± 0.34 | 90.24 ± 0.35 | 94.12 ± 0.96 |
| SimMIM | IN→CXR(926K) | 88.37 ± 0.40 | 83.04 ± 0.15 | 74.08 ± 0.39 | 91.71 ± 1.04 | 95.76 ± 1.79 |
| Ark-5(ours) | IN→CXR(335K) | 88.73 ± 0.20 | 82.87 ± 0.13 | 74.73 ± 0.59 | 94.67 ± 0.33 | 98.92 ± 0.21 |
| Ark-6(ours) | IN→CXR(704K) | **89.14 ± 0.22** | **83.05 ± 0.09** | **74.76 ± 0.35** | **95.07 ± 0.16** | **98.99 ± 0.16** |

| | | Segmentation task | | | | |
|---|---|---|---|---|---|---|
| Initialization | Pretraining | 7.NIHM | 8.JSRT Lung | 8.JSRT Heart | 8.JSRT Clavicle | 9.VINR |
| Random | — | 96.32 ± 0.18 | 96.82 ± 0.10 | 92.55 ± 0.28 | 85.56 ± 0.71 | 56.48 ± 0.02 |
| Supervised | IN | 97.23 ± 0.09 | 97.13 ± 0.07 | 92.58 ± 0.29 | 86.94 ± 0.69 | 62.40 ± 0.80 |
| SimMIM | IN | 97.12 ± 0.14 | 96.90 ± 0.08 | 93.75 ± 0.11 | 87.18 ± 0.63 | 61.64 ± 0.60 |
| SimMIM | IN→CXR(926K) | 97.10 ± 0.40 | 96.93 ± 0.12 | 93.75 ± 0.36 | 88.87 ± 1.06 | 63.46 ± 0.80 |
| Ark-5(ours) | IN→CXR(335K) | 97.65 ± 0.17 | 97.41 ± 0.04 | 94.16 ± 0.66 | 90.01 ± 0.35 | **63.96 ± 0.30** |
| Ark-6(ours) | IN→CXR(704K) | **97.68 ± 0.03** | **97.48 ± 0.08** | **94.62 ± 0.16** | **90.05 ± 0.15** | 63.70 ± 0.23 |

Results and Analysis: As shown in Table 2, Ark models consistently outperform the SOTA fully/self-supervised ImageNet pretrained models on all target tasks. These results highlight the benefit of leveraging additional domain-relevant data in pretraining to reduce the domain gap and further improve the model's performance on target tasks. Furthermore, compared with the self-supervised domain-adapted model that utilizes 926K CXRs for pretraining, Ark models yield significantly superior performance on Dataset 1, 3-5 with only 335K CXRs, and on-par performance on 2.NIHC with 704K CXRs. These results demonstrate the superiority of Ark that accrues and reuses the knowledge retained in heterogeneous expert annotations from multiple datasets, emphasizing the importance of learning from expert labels. Moreover, it is observed that Ark-6 consistently outperforms Ark-5, indicating the importance of incorporating more data and annotations from diverse datasets in pretraining.

2) Ark Provides Generalizable Representations for Segmentation Tasks.

Experimental Setup: To evaluate the generalizability of Ark's representations, the Ark models are transferred to five segmentation tasks involving lungs, heart, clavicles, and ribs, and their performance compared with three SOTA fully/self-supervised models. The segmentation network is built upon UperNet, which consists of a backbone network, a feature pyramid network, and a decoder network. The backbone network is implemented with Swin-B and initialized with the pretrained weights from the Ark and the above mentioned SOTA models. The remaining networks are randomly initialized. All layers in the segmentation models are then fine-tuned under the same experimental setup.

Results and Analysis: As seen in Table 2, Ark models achieve significantly better performance than the SOTA models, demonstrating that Ark learned generalizable representations for delineating organs and bones in CXR. This superior performance is achieved by pretraining using large-scale CXRs and various disease labels from diverse datasets. Clinically, certain thoracic abnormalities can be diagnosed by examining the edges of the lungs, heart, clavicles, or ribs in CXR. For instance, a pneumothorax can be detected by observing a visible "visceral pleural line" along part or the entire length of the lateral chest wall. Cardiomegaly can be diagnosed when the heart appears enlarged, with maximum diameter of the heart exceeding a pre-defined cardiothoracic ratio. Fractures can be identified when the edges of the clavicles or ribs appear abnormally displaced or the bone cortex appears offset. Therefore, leveraging diagnostic information from disease labels during pretraining enables Ark models to better capture the nuanced and varied pathological patterns, strengthening the models' ability to represent anatomically specific features that reflect abnormal conditions in various organs or bones. By contrast, the SimMIM (IN→CXR (926K)) model is pretrained with a self-supervised masked image modeling proxy task, which may use many clues to reconstruct the masked patches that are not necessarily related to pathological conditions, leading to lower performance despite training on more images.

3) Ark Offers Embeddings with Superior Quality Over Google CXR-FM.

Experimental Setup: To highlight the benefits of learning from more detailed diagnostic disease labels, Ark models are compared with Google CXR-FM.

CXR-FM was trained on a large dataset of 821,544 CXRs from three different sources, but with coarsened labels (normal or abnormal). By contrast, Ark models are trained with less data, but aims to fully utilize all labels provided by experts in the original datasets. Furthermore, Ark models employ a much smaller backbone (88M parameters) compared with CXR-FM using EfficientNet-L2 (480M parameters). Since Google CXR-FM is not released and cannot be fine-tuned, its released API was used to generate the embeddings (information-rich numerical vectors) for all images in the target tasks. For the sake of fairness, the embeddings were generated from Ark's projector, whose dimension is the same as Google's. To evaluate the quality of the learned representations of these models, linear probing was conducted by training a simple linear classifier for each target task. The performance of both models is evaluated on six target tasks, including an unseen dataset, 10.SIIM, where the images have not been previously seen by the Ark models during pretraining. Additionally, the same evaluation is performed on 10.SIIM with partial training sets or even few-shot samples to further demonstrate the high quality of Ark models' embeddings.

Results and Analysis: FIG. 2A shows that Ark-6 outperforms CXR-FM significantly on Dataset 1, 2, 5 and 10, and performs comparably to CXR-FM on 3.RSNA. Similarly, Ark-5 performs better than CXR-FM on Dataset 1, 5 and 10, while performing comparably on the remaining tasks. Moreover, FIG. 2B shows that both Ark-5 and Ark-6 consistently outperform CXR-FM in small data regimes, highlighting the superiority of Ark's embeddings, which carry richer information that can be utilized more efficiently. These results demonstrate that Ark models learn higher-quality representations with less pretraining data while employing a much smaller backbone than CXR-FM, highlighting that learning from more granular diagnostic labels, such as Ark, is superior to learning from coarsened normal/abnormal labels.

4) Ark Shows a Lower False-Negative Rate (FNR) and Less Gender Bias.

Experimental Setup: Underdiagnosis, as indicated by false-negative results, may lead to delayed treatment, resulting in severe consequences. Moreover, population imbalanced data may train models of biases, adversely affecting diagnostic performance in minority populations. Therefore, a robust computer-aided diagnosis (CAD) system should provide a low false-negative rate and strong resilience to biased training data. To demonstrate Ark's robustness relative to Google CXR-FM, their gender-based FNRs are examined on 1.CXPT and 2.NIHC, as these two datasets offer sufficient cases with gender information. Further investigation of gender biases is performed in Ark-6 and CXR-FM on 1.CXPT using gender-exclusive training sets by following the setup in Larrazabal, A. J., Nieto, N., Peterson, V., Milone, D. H., Ferrante, E., Gender imbalance in medical imaging datasets produces biased classifiers for computer-aided diagnosis, Proceedings of the National Academy of Sciences 117 (23), 12592-12594 (2020). Their training/test splits are used to ensure a balanced number of cases per class in 40 male/female-only folds, train linear classifiers on those folds using embeddings from Ark-6 and CXR-FM, and then evaluate these classifiers on the corresponding male/female-only test splits. A model, if biased, will perform differently when its training and test data are of the opposite gender. This setup is detailed in the experimental details set forth in section E below.

Results and Analysis: FIG. 3A illustrates that Ark models have lower FNRs than CXR-FM for both genders on both tasks, demonstrating that Ark models are less likely to underdiagnose disease conditions than CXR-FM. In FIG. 3B, the biases in the pretrained models are measured by performance differences between linear classifiers trained on male-only and female-only embeddings. The upper part of FIG. 3B depicts the results of testing on female-only sets, where the classifiers trained on male-only embeddings generally perform poorly compared with those trained on female embeddings, revealing gender biases due to data imbalance. Among the 12 diseases, the classifiers trained with Google's embeddings have unbiased performances for only four diseases, whereas those using Ark-6's embeddings perform in an unbiased fashion with no significant differences for the eight diseases. The same situation occurs when testing is performed on male patients as shown in the lower part of FIG. 3B. The gender bias analysis demonstrates that Ark has greater robustness to the extremely imbalanced data that contributes to gender bias in computer-aided diagnosis.

Supplementary Material

This supplementary material provides further details regarding embodiments of the invention. It is organized as follows. Section A presents a comprehensive list of diagnostic labels from different public datasets, revealing marked label heterogeneity across institutions. Section B offers a comparison between Ark and other existing works concerning the assembly of public datasets, emphasizing Ark's label-agnostic and task-scalable advantages. Section C includes ablation studies that demonstrate the necessity of the projector and consistency loss, along with the superiority of the teacher model. Sections D and E present pseudocode for Ark's cyclic pretraining and elaborate on the experimental setups.

A. Heterogeneous Labels

Table 3. As listed in this table, datasets created at different institutions tend to be annotated differently even when addressing the same clinical issue. Ark aims to accrue and reuse expert knowledge from heterogeneous labels with numerous public datasets to pretrain generic source models that are more robust, generalizable, and transferable to application-specific target tasks, demonstrating superior and robust performance over the SOTA fully/self-supervised baselines (Table 2) and Google CXR-FM (FIG. 2A, 2B). The challenge of learning from heterogeneous labels is addressed in Ark via multi-task heads and cyclic pretraining (FIG. 1).

TABLE 3

| Dataset | Inconsistencies in diagnostic labels associated with popular public X-rays datasets |
|---|---|
| 1. CXPT<br>6. MMIC | No Finding, Enlarged Cardiomediastinum, Cardiomegaly, Lung Opacity, Lung Lesion, Edema, Consolidation, Pneumonia, Atelectasis, Pneumothorax, Pleural Effusion, Pleural Other, Fracture, Support Devices |
| 2. NIHC | Atelectasis, Cardiomegaly, Effusion, Infiltration, Mass, Nodule, Pneumonia, Pneumothorax, Consolidation, Edema, Emphysema, Fibrosis, Pleural Thickening, Hernia |
| 3. RSNA | Normal, No Lung Opacity/Not Normal, Lung Opacity |
| 4. VINC | Pleural Effusion, Lung Tumor, Pneumonia, Tuberculosis, Other Diseases, No Finding |
| 5. NIHS | Tuberculosis |

B. Other Works for Assembling Public Datasets

Table 4. Ark is dataset/task-agnostic as it does not require prior label "understanding" of public datasets. Unlike the listed example works that need to manually assemble the labels into a pre-defined list and train a dynamic controller/adapter as directives for different: tasks, Ark is designed with pluggable multi-task heads and cyclic pretraining (section 2) to offer flexibility and scalability for adding new tasks without manually consolidating heterogeneous labels or training task-specific controllers/adapters.

TABLE 4

| Related works | How to preprocess labels? | When a new task comes? |
|---|---|---|
| Label-Assemble[1] | Need a pre-defined label list | Update the label list and retrain the adapter if any labels aren't in the original list |

TABLE 4-continued

| Related works | How to preprocess labels? | When a new task comes? |
|---|---|---|
| DoDNet[2] | Need a pre-defined task list | Renew the task list and retrain the controller when adding new tasks |
| CLIP-diven[3] | Need manual designs of prompt to get CLIP embeddings | Re-generate the CLIP embedding for any new classes and retrain the controller |

TABLE 4-continued

| Related works | How to preprocess labels? | When a new task comes? |
|---|---|---|
| Ark | Task-agnostic, use all readily-accessible labels directly as they are | Plug in Ark a new head, independent from existing tasks, for the new task, no modification on the rest architecture |

C. Ablation Study

Table 5. Ablation studies on Ark-5 via linear probing show the projector and consistency loss are essential and the teacher significantly outperforms the student.

TABLE 5

| Model | Projector | $\mathcal{L}_{consist}$ | 2.NIHC | 3.RSNA | 4.VINC | 5.NIHS |
|---|---|---|---|---|---|---|
| Teacher | x | x | 81.09 ± 0.08 | 74.21 ± 0.42 | 94.89 ± 0.07 | 98.81 ± 0.25 |
| Teacher | x | ✓ | 81.19 ± 0.05 | 74.42 ± 0.25 | 95.24 ± 0.08 | 99.01 ± 0.08 |
| Student | ✓ | ✓ | 81.34 ± 0.04 | 74.12 ± 0.11 | 94.85 ± 0.07 | 99.17 ± 0.07 |
| Teacher | ✓ | ✓ | **81.39 ± 0.02** | **74.74 ± 0.19** | **95.35 ± 0.04** | **99.41 ± 0.03** |

D. Pseudocode for Ark's Cyclic Pretraining

As illustrated in FIG. 1 and described in Algorithm 1, Ark is built on a teacher-student model, whose student is augmented with multi-task heads (each corresponding to one task) and trained via cyclic pretraining. Cyclic pretraining is an iterative process. At each iteration, the student aims to accrue knowledge from every expert annotation through its corresponding task head by sequentially scanning all datasets (tasks) one by one for one epoch. At the end of each task, the accrued knowledge is accumulated into the teacher (via EMA) and reused to help accrue more knowledge from the expert annotations associated with the next dataset. To reinforce the feedback loop between the student and teacher, after their encoders, a projector is introduced to map the representations to the same feature space via the consistency loss, also serving as the embedding for linear probing in the evaluation. After pretraining, the accumulated knowledge in the teacher is reused and transferred to the application-specific target tasks.

Algorithm 1:
A round of Ark's cycle pretraining

```
Data: Datasets: D = {D_1, D_2, . . . , D_n}; Sample: image- label pair
(x, y) ∈ D_1
Functions: Data augmentation: τ_1(•),τ_2(•); Dataset/task-specific losses:
       [ℒ_D1(•,•), ℒ_D2(•,•), . . . , ℒ_Dn(•,•)]; Consistency
       loss: ℒ_const(•,•);
       Loss update by SGD optimizer: Update_sgd(•,•)
Trainable Parameters: Student's encoder and projector: e_s, p_s;
              Multi-task heads ℋ = {h_1, h_2, . . . , h_n}
Stop Gradient: Teacher's encoder and projector: e_t, p_t
Hyperparameters: Momentum: λ
1      {e_t, p_t} ← {e_s, p_s} // initialize teachers with student's parameter
2      for D_i, in D_1, D_2, . . . , D_n do
         /* train student for one epoch                                  */
3  |     for (x, y) in D_i do
4  | |     x' = τ_1 (x)
5  | |     x" = τ_2 (x')
6  | |     emb_t, emb_s = p_t(e_t(x')), p_s(e_s(x"))
7  | |       pred = h_i(emb_s)
8  | |       Loss = ℒ_Di (pred, y) + ℒ_const(emb_t, emb_s)
9  | |__     Update ({e_s, p_s, h_i}, Loss)
   |     /* Update teacher by student's parameters via epoch-wise EMA     */
10 | _   {e_t, p_t} ← λ {e_t, p_t} + (1 − λ){e_s, p_s}
```

E. Experiment Details

Pretraining: Ark-5/6 was trained with 335,484/704,363 chest X-rays from the first 5/6 datasets in Table 1 collected by 5/6 different institutions around the world and annotated by their experts. The originally provided labels were used (Table 3), showing marked differences across institutions. To avoid test-image leaks, all validation and test data are excluded from the Ark pretraining. A base version of the Swin transformer was employed with an input resolution of 224×224 as the backbone. The encoders in teacher and student are initialized with the officially released weights trained on ImageNet, and the projectors and the multi-task heads are randomly initialized. The task-specific (classification) loss is associated with each dataset based on its labels. A binary cross-entropy is used for the binary/multi-label classification tasks (Dataset 1-2, 4-6) and cross-entropy for the multi-class classification task (Dataset 3). Besides, mean-squared error is used for the consistency loss. The student model is optimized using SGD optimizer with an initial learning rate of 0.3, and a batch size of 200 distributed across 4 Nvidia V100 GPUs with a memory of 32 GB per-card; a stop-gradient operator is applied on the teacher and updated using epoch-wise EMA of the student parameters at the end of each task with an initial momentum of 0.9. The image augmentation function $T_1$ (.) include random cropping and rotation, and $T_2$ (.) includes randomly changing brightness, contrast, and Gamma distribution of an image.

Evaluation: Ark-5 and Ark-6 are evaluated via transfer learning and compared with SOTA fully-supervised and self-supervised models (Table 2). For fair comparisons, the SoTA2 is followed and applied with the same augmentations for all methods. The performance of binary/multi-label classification is measured by AUC (area under the ROC curve), multi-class classification by accuracy, and segmentation by Dice. At least ten trials were performed, and the mean and standard deviation of the performance metrics reported, and statistical analysis based on an independent two-sample t-test was further presented.

To provide a more comprehensive evaluation, a linear probing was conducted (FIG. 2A, 2B) and gender biases analyzed (FIG. 3A, 3B) on the Ark models in comparison with Google CXR-FM. The embeddings were pre-generated for all images in the target tasks from Ark-5, Ark-6 and Google CXR-FM3, and then a simple linear classifier for each target task was trained.

The evaluation of gender bias robustness for each model follows the above-mentioned linear probing protocol. The FNRs are computed in terms of gender using the linear probing results on 1.CXPT and 2.NIHC. Note that gender biases could not be analyzed on datasets 3, 4, and 10 because they do not come with patient genders. Furthermore, to analyze the gender biases in the Ark model and CXR-FM, the train/test splits in the GenderBias_CheXNet repository4 were followed to ensure a balanced number of cases per class in the 20 male-only and 20 female-only folds, where the labels "No Finding" and "Support Device" are excluded. 40 linear classifiers are trained on the male-only and female-only splits using embeddings from Ark-6 and CXR-FM to evaluate their gender biases. These classifiers are then evaluated on the corresponding male/female-only test splits and the average performance over the 20 folds is reported.

Table 6 lists the key setups used in Ark's pretraining and evaluation protocols.

TABLE 6

| Ark pretraining setup | |
|---|---|
| Backbone | Swin Transformer Base (input resolution: 224 × 224) |
| Initialization | Encoders: officially released ImageNet weights<br>Projectors and Multi-task heads: random weights |
| Loss function | Task-specific loss: binary cross-entropy (BCE) for Dataset 1-2, 4-6<br>cross-entropy (CE) for Dataset 3<br>Consistency loss: mean-squared error (MSE) |
| Optimization | Student: SCD optimizer, learning rate of 0.3, Cosine scheduler<br>Teacher: Stop gradient, EMA update, momentum of 0.9 |
| Pretraining | 200 rounds (iterates through all datasets 200 times) |
| Augmentation | $\tau_1$(.): Random cropping and rotation<br>$\tau_2$(.): Random changing of image brightness, contrast, and Gamma distribution |
| Devices | 4 Nvidia V100 CPUs (32 GB) |
| **Ark evaluation setup** | |
| Tranferred model | Teacher's encoder |
| Embeddings | Pre-generated from Ark's projector with a dimension of 1 × 1376 |
| Metrics | Binary/Multi-label classification: Area under the ROC curve (AUC)<br>Multi-class classification: Accuracy (ACC)<br>Segmentation: Dice similarity coefficient (Dice) |
| Performance | Mean and Standard Deviation of the metrics for 10 trials |
| Significance test | Independent two-sample t-test (p-value < 0.05) |

Conclusions and Future Work

Foundation Ark, the first open foundation model, was developed to realize a vision: accruing and reusing knowledge retained in heterogeneous expert annotations with numerous datasets offers superior and robust performance. Experimental results are strong on CXRs, and there are plans to extend Ark to other modalities. It is hoped that Ark's performance encourages researchers worldwide to share codes and datasets big or small for creating open foundation models, accelerating open science, and democratizing deep learning for medical imaging.

In addition to various hardware components described herein, embodiments further include various operations. The operations described in accordance with such embodiments may be performed by hardware components or may be embodied in machine-executable instructions, which may be used to cause a specialized and special-purpose processor having been programmed with the instructions to perform the operations described herein. Alternatively, the operations may be performed by a combination of hardware and software. In such a way, the embodiments of the invention provide a technical solution to a technical problem.

Embodiments also relate to an apparatus for performing the operations disclosed herein. This apparatus may be specially constructed for the required purposes, or it may be a special purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

While the algorithms and displays presented herein are not inherently related to any particular computer or other apparatus, they are specially configured and implemented via customized and specialized computing hardware which is specifically adapted to more effectively execute the novel algorithms and displays. Various customizable and special purpose systems may be utilized in conjunction with specially configured programs in accordance with the teachings herein, or it may prove convenient, in certain instances, to construct a more specialized apparatus to perform the required method steps. In addition, embodiments are not described with reference to any particular programming language. It will be appreciated that a variety of programming languages may be used to implement the teachings of the embodiments as described herein.

Embodiments may be provided as a computer program product, or software, that may include a machine-readable medium having stored thereon instructions, which may be used to program a computer system (or other electronic devices) to perform a process according to the disclosed embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical), etc.

Any of the disclosed embodiments may be used alone or together with one another in any combination. Although various embodiments may have been partially motivated by deficiencies with conventional techniques and approaches, some of which are described or alluded to within the specification, the embodiments need not necessarily address or solve any of these deficiencies, but rather, may address only some of the deficiencies, address none of the deficiencies, or be directed toward different deficiencies and problems which are not directly discussed.

It is appreciated that a machine in the exemplary form of a computer system, in accordance with one embodiment, includes a set of instructions that may be executed to cause the machine/computer system to perform any one or more of the methodologies discussed herein.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while the machine may be a single machine, the term "machine" shall also be taken to include any collection of machines (e.g., computers) that individually or jointly execute a set (or multiple sets) of instructions to perform any one or more of the methodologies discussed herein.

An exemplary computer system includes a processor, a main memory (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory (e.g., a persistent storage device including hard disk drives and a persistent database and/or a multi-tenant database implementation), which communicate with each other via a bus. Main memory includes an encoder-decoder network (e.g., such as an encoder-decoder implemented via a neural network model) for performing operations including processing medical imaging in support of the methodologies and techniques described herein. Main memory and its sub-elements are further operable in conjunction with processing logic and processor to perform the methodologies discussed herein.

Processor represents one or more specialized and specifically configured processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor may also be one or more special-purpose processing devices such as an application-specific integrated circuit (ASIC), a field programmable gate array (FPGA), a digital signal processor (DSP), network processor, or the like. The processor is configured to execute the processing logic for performing the operations and functionality discussed herein.

The computer system may further include a network interface card. The computer system also may include a user interface (such as a video display unit, a liquid crystal display, etc.), an alphanumeric input device (e.g., a keyboard), a cursor control device (e.g., a mouse), and a signal generation device (e.g., an integrated speaker). The computer system may further include peripheral device (e.g., wireless or wired communication devices, memory devices, storage devices, audio processing devices, video processing devices, etc.).

The secondary memory may include a non-transitory machine-readable storage medium or a non-transitory computer readable storage medium or a non-transitory machine-accessible storage medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable storage media. The software may further be transmitted or received over a network via the network interface card.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

REFERENCES

1. Rsna pneumonia detection challenge (2018), www.kaggle.com/c/rsna-pneumonia-detection-challenge
2. Siim-acr pneumothorax segmentation (2019), kaggle.com/competitions/siim-acr-pneumothorax-segmentation
3. Collins, J.: Chest wall trauma. Journal of thoracic imaging 15 (2), 112-119 (2000)
4. Irvin, J., Rajpurkar, P., Ko, M., Yu, Y., Ciurea-Ilcus, S., Chute, C., Marklund, H., Haghgoo, B., Ball, R., Shpanskaya, K., et al.: Chexpert: A large chest radiograph dataset with uncertainty labels and expert comparison. In: Proceedings of the AAAI conference on artificial intelligence. vol. 33, pp. 590-597 (2019)
5. Jaeger, S., Candemir, S., Antani, S., Wáng, Y. X. J., Lu, P. X., Thoma, G.: Two public chest x-ray datasets for computer-aided screening of pulmonary diseases. Quantitative imaging in medicine and surgery 4 (6), 475 (2014)
6. Johnson, A. E., Pollard, T. J., Berkowitz, S. J., Greenbaum, N. R., Lungren, M. P., Deng, C.y., Mark, R. G., Horng, S.: Mimic-cxr, a de-identified publicly available database of chest radiographs with free-text reports. Scientific data 6 (1), 1-8 (2019)
7. Kemker, R., McClure, M., Abitino, A., Hayes, T., Kanan, C.: Measuring catas-trophic forgetting in neural networks. In: Proceedings of the AAAI conference on artificial intelligence. vol. 32 (2018)
8. Larrazabal, A. J., Nieto, N., Peterson, V., Milone, D. H., Ferrante, E.: Gender im-balance in medical imaging datasets produces biased classifiers for computer-aided diagnosis. Proceedings of the National Academy of Sciences 117 (23), 12592-12594 (2020)
9. Liu, Z., Lin, Y., Cao, Y., Hu, H., Wei, Y., Zhang, Z., Lin, S., Guo, B.: Swin transformer: Hierarchical vision transformer using shifted windows. In: Proceedings of the IEEE/CVF International Conference on Computer Vision. pp. 10012-10022 (2021)
10. Ma, D., Hosseinzadeh Taher, M. R., Pang, J., Islam, N. U., Haghighi, F., Gotway, M. B., Liang, J.: Benchmarking and boosting transformers for medical image classification. In: Domain Adaptation and Representation Transfer. pp. 12-22. Springer Nature Switzerland, Cham (2022)
11. Mason, R. J., Broaddus, V. C., Martin, T. R., King, T. E., Schraufnagel, D., Murray, J. F., Nadel, J. A.: Murray and Nadel's Textbook of Respiratory Medicine E-Book: 2-Volume Set. Elsevier Health Sciences (2010)
12. McMahan, B., Moore, E., Ramage, D., Hampson, S., y Arcas, B. A.: Communication-efficient learning of deep networks from decentralized data. In: Artificial intelligence and statistics. pp. 1273-1282. PMLR (2017)
13. Nguyen, H. Q., Lam, K., Le, L. T., Pham, H. H., Tran, D. Q., Nguyen, D. B., Le, D. D., Pham, C. M., Tong, H. T., Dinh, D. H., et al.: Vindr-cxr: An open dataset of chest x-rays with radiologist's annotations. Scientific Data 9 (1), 429 (2022)
14. Nguyen, H. C., Le, T. T., Pham, H. H., Nguyen, H. Q.: Vindr-ribcxr: A benchmark dataset for automatic segmentation and labeling of individual ribs on chest x-rays. In: Medical Imaging with Deep Learning (2021)
15. Peng, Y., Wang, X., Lu, L., Bagheri, M., Summers, R., Lu, Z.: Negbio: a high-performance tool for negation and uncertainty detection in radiology reports. AMIA Summits on Translational Science Proceedings 2018, 188 (2018)
16. Sellergren, A. B., Chen, C., Nabulsi, Z., Li, Y., Maschinot, A., Sarna, A., Huang, J., Lau, C., Kalidindi, S. R., Etemadi, M., et al.: Simplified transfer learning for chest radiography models using less data. Radiology 305 (2), 454-465 (2022)
17. Shiraishi, J., Katsuragawa, S., Ikezoe, J., Matsumoto, T., Kobayashi, T., Komatsu, K.i., Matsui, M., Fujita, H., Kodera, Y., Doi, K.: Development of a digital image database for chest radiographs with and without a lung nodule: receiver operating characteristic analysis of radiologists' detection of pulmonary nodules. American Journal of Roentgenology 174 (1), 71-74 (2000)
18. Tarvainen, A., Valpola, H.: Mean teachers are better role models: Weight-averaged consistency targets improve semi-supervised deep learning results. Advances in neural information processing systems 30 (2017)
19. Wang, X., Peng, Y., Lu, L., Lu, Z., Bagheri, M., Summers, R. M.: Chestx-ray8: Hospital-scale chest x-ray database and benchmarks on weakly-supervised classification and localization of common thorax diseases. In: Proceedings of the IEEE conference on computer vision and pattern recognition. pp. 2097-2106 (2017)
20. Xiao, T., Liu, Y., Zhou, B., Jiang, Y., Sun, J.: Unified perceptual parsing for scene understanding. In: Proceedings of the European conference on computer vision (ECCV). pp. 418-434 (2018)
21. Xie, Z., Zhang, Z., Cao, Y., Lin, Y., Bao, J., Yao, Z., Dai, Q., Hu, H.: Simmim: A simple framework for masked image modeling. In: Proceedings of the IEEE/CVF Conference on Computer Vision and Pattern Recognition. pp. 9653-9663 (2022)
22. Zhu, Z., Kang, M., Yuille, A., Zhou, Z.: Assembling existing labels from public datasets to diagnose novel diseases: Covid-19 in late 2019. NeurIPS Workshop on Medical Imaging meets NeurIPS (2022)

What is claimed is:

1. A system comprising:

a memory to store instructions;

a processor to execute the instructions stored in the memory;

wherein the system is specially configured to execute instructions for accruing and reusing knowledge by a trained artificial intelligence (AI) model for use with medical image classification, in the context of medical image analysis, by performing the following operations:

receiving medical image data at the system from a plurality of datasets provided via publicly available sources;

evaluating the medical image data for the presence of expert notation embedded within the medical image data;

determining the expert notations embedded within the medical image data are formatted using inconsistent and heterogeneous labeling across the plurality of datasets;

generating an interim AI model by applying a task head classifier to learn annotations of the expert notations embedded within the medical image data to generate an interim AI model;

scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objectives;

training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

2. The system of claim 1, further comprising:

generating a new pre-trained AI model specially configured for a new application-specific target task by applying cyclic training of the new pre-trained AI model for the new application-specific target task; and wherein the cyclic training iteratively repeats the training of the pre-trained AI model previously trained against the first application-specific target task.

3. The system of claim 2 wherein model degradation is mitigated by re-applying task re-visitation training forcing the new pre-trained AI model being trained to re-visit all tasks in each round of training and forcing the new pre-trained AI model being trained to re-use all accrued knowledge to improve learning by the first pre-trained AI model for the first application-specific target task as improving learning for the new pre-trained AI model specifically configured for the new application-specific target task.

4. A computer-implemented method performed by a system having at least a processor and a memory therein to execute instructions for accruing and reusing knowledge by a trained artificial intelligence (AI) model for use with medical image classification, in the context of medical image analysis, by performing the following operations:

receiving medical image data at the system from a plurality of datasets provided via publicly available sources;

evaluating the medical image data for the presence of expert notation embedded within the medical image data;

determining the expert notations embedded within the medical image data are formatted using inconsistent and heterogeneous labeling across the plurality of datasets;

generating an interim AI model by applying a task head classifier to learn the annotations of the expert notations embedded within the medical image data to generate an interim AI model;

scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objectives;

training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

5. The computer-implemented method of claim 4, further comprising:

generating a new pre-trained AI model specially configured for a new application-specific target task by applying cyclic training of the new pre-trained AI model for the new application-specific target task; and wherein the cyclic training iteratively repeats the training of the pre-trained AI model previously trained against the first application-specific target task.

6. The computer-implemented method of claim 5 wherein model degradation is mitigated by re-applying task re-visitation training forcing the new pre-trained AI model being trained to re-visit all tasks in each round of training and forcing the new pre-trained AI model being trained to re-use all accrued knowledge to improve learning by the first pre-trained AI model for the first application-specific target task as improving learning for the new pre-trained AI model specifically configured for the new application-specific target task.

7. A non-transitory computer readable storage media having instructions stored thereupon that, when executed by a system having at least a processor and a memory therein, the instructions cause the processor to execute instructions for accruing and reusing knowledge by a trained artificial intelligence (AI) model for use with medical image classification, in the context of medical image analysis, by performing the following operations:

receiving medical image data at the system from a plurality of datasets provided via publicly available sources;

evaluating the medical image data for the presence of expert notation embedded within the medical image data;

determining the expert notations embedded within the medical image data are formatted using inconsistent and heterogeneous labeling across the plurality of datasets;

generating an interim AI model by applying a task head classifier to learn annotations of the expert notations embedded within the medical image data to generate an interim AI model;

scaling the interim AI model having the learned annotations of the expert notations embedded therein to additional tasks by applying multi-task heads using cyclical pre-training of the interim AI model trained previously to generate task-specific AI models, with each respective task-specific AI model having differently configured task-specific learning objectives;

training a pre-trained AI model specially configured for an application-specific target task by applying task re-visitation training forcing the pre-trained AI model being trained to re-visit all tasks in each round of training and forcing the pre-trained AI model being trained to re-use all accrued knowledge to improve learning by the pre-trained AI model being trained against the current application-specific target task for which the pre-trained AI model is being trained.

8. The non-transitory computer readable storage media of claim 7, further comprising:

generating a new pre-trained AI model specially configured for a new application-specific target task by applying cyclic training of the new pre-trained AI model for the new application-specific target task; and wherein the cyclic training iteratively repeats the training of the pre-trained AI model previously trained against the first application-specific target task.

9. The non-transitory computer readable storage media of claim 8 wherein model degradation is mitigated by re-applying task re-visitation training forcing the new pre-trained AI model being trained to re-visit all tasks in each round of training forcing the new pre-trained AI model being trained to re-use all accrued knowledge to strengthen learning by the first pre-trained AI model for the first application-specific target task as strengthening learning for the new pre-trained AI model specifically configured for the new application-specific target task.

* * * * *